United States Patent [19]

Hefner, Jr. et al.

[11] Patent Number: 4,640,957
[45] Date of Patent: Feb. 3, 1987

[54] POLYIMIDO-ESTER COMPOUNDS AND THERMOSET RESIN COMPOSITIONS CONTAINING SAME

[75] Inventors: Robert E. Hefner, Jr.; Douglas L. Hunter, both of Lake Jackson, Tex.

[73] Assignee: The Dow Chemical Company, Midland, Mich.

[21] Appl. No.: 744,188

[22] Filed: Jun. 13, 1985

Related U.S. Application Data

[62] Division of Ser. No. 562,333, Dec. 16, 1983, Pat. No. 4,560,768.

[51] Int. Cl.$^4$ .............. C08L 67/06; C08L 77/12; C08L 63/10
[52] U.S. Cl. .............................. 525/44; 525/47; 525/421; 525/502; 525/531; 526/259
[58] Field of Search .......... 525/421, 44, 47, 502, 525/531, 421; 526/259

[56] References Cited

U.S. PATENT DOCUMENTS 4,435,530  3/1984  Hefner ............... 523/512
4,496,688  1/1985  Hefner ............... 525/44
4,560,768  12/1985  Hefner ............... 548/548

Primary Examiner—John C. Bleutge
Assistant Examiner—Patricia Short
Attorney, Agent, or Firm—Benjamin G. Colley

[57] ABSTRACT

Polyimido-ester compounds having the formula RO-C(O)-R$_1$-C(O)-OR are disclosed wherein R is an alkylene N-dicarboximido radical containing cycloolefinic unsaturation and R$_1$ is the divalent residue of an unsaturated polycarboxylic acid such as fumaric, itaconic, aconitic, mesaconic, or glutaconic acid. These compounds are blended with unsaturated resins such as unsaturated polyester resin or vinyl ester resin, and polymerizable unsaturated monomers such as styrene to provide thermosettable resin compositions which can be cured to provide castings or laminates with improved resistance to thermal aging.

6 Claims, No Drawings

POLYIMIDO-ESTER COMPOUNDS AND THERMOSET RESIN COMPOSITIONS CONTAINING SAME

This is a divisional application Ser. No. 562,333, filed Dec. 16, 1983 now U.S. Pat. No. 4,560,768.

BACKGROUND OF THE INVENTION

The present invention pertains to new polyimidoesters of unsaturated polycarboxylic acids and thermosettable resin compositions containing the polyimidoesters.

Thermosettable compositions such as unsaturated polyester resins, dicyclopentadiene modified unsaturated polyester resins, unsaturated polyesteramide resins, dicyclopentadiene modified unsaturated polyesteramide resins, vinyl ester resins and the like are well known. Such resins can be employed as is, but are usually diluted with a polymerizable unsaturated monomer such as styrene. These resins are useful in the preparation of castings, laminates, coatings, and the like. However, such resins have limitations on their resistance to thermal aging, thus limiting their use.

Vinyl ester resins have been blended with dicyclopentadienyl esters of an unsaturated polycarboxylic acid as set forth in U.S. Pat. No. 4,450,634 filed Oct. 12, 1982.

Norbornyl modified unsaturated polyesters or polyesteramides have been blended with dicyclopentadienyl esters of an unsaturated polycarboxylic acid as set forth in U.S. Pat. No. 4,435,530 filed Oct. 22, 1982.

Unsaturated polyesters or polyesteramides have been blended with dicyclopentadienyl esters of an unsaturated polycarboxylic acid as set forth in U.S. Pat. No. 4,496,688 filed Mar. 21, 1983.

SUMMARY OF THE INVENTION

The present invention is a polyimido-ester compound having the formula:

$$R-O-\overset{O}{\underset{\|}{C}}-R_1-\overset{O}{\underset{\|}{C}}-O-R$$

wherein R is selected from one of the following groups

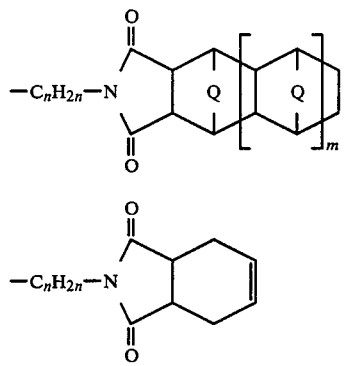

and $R_1$ is a divalent radical selected from one of the following groups
I. —C(X)=CH—
II. —CH$_2$—C(=Y)—
III. —CH=C(Z)—CH$_2$—
wherein
n=1–6
m=0–10
X=hydrogen or methyl
Y=methylene or isopropylidene
Z=hydrogen or —COOR
Q=methylene A further aspect of the present invention is a resin composition which is thermosettable upon curing with a curing quantity of a suitable curing agent such as free radical forming catalysts, which thermosettable composition comprises, (A) from about 5 to about 95, percent by weight (pbw) based on the total composition weight of at least one resin composition selected from the group consisting of (a) unsaturated polyester resins, (b) unsaturated polyesteramide resins, (c) dicyclopentadiene modified unsaturated polyester resins, (d) dicyclopentadiene modified unsaturated polyesteramide resins, and (e) vinyl ester resins, (B) from about 5 to about 95, percent by weight of at least one polymerizable ethylenically unsaturated monomer; and (C) from about 1 to about 70, percent by weight of an imido bis or tris ester of an unsaturated di or tricarboxylic acid having the above formula.

The preferred amounts of the resin in (A) above are from about 20 to about 80 percent by weight and most preferably from about 45 to about 70 percent by weight. The preferred amounts of the unsaturated monomer in (B) above are from about 20 to about 70 and most preferably from about 30 to about 55 percent by weight. The preferred amounts of the imido unsaturated polyester in (C) above are from about 3 to about 40 percent by weight and most preferably from about 15 to about 30 percent by weight.

The present invention thus provides new polyimidoester compounds which are useful to make a thermosettable resin composition which has improved resistance to thermal aging without an unacceptable reduction in other mechanical properties. The cured resin in many instances has an improvement in one or more properties such as heat distortion temperature, hardness, flexural strength, flexural modulus and the like.

DETAILED DESCRIPTION OF THE INVENTION

The norbornyl (dicyclopentadiene) modified unsaturated polyesteramides used herein can be prepared by the methods described herein and they are further described in U.S. Pat. No's. 4,409,371 and 4,410,686.

The norbornyl modified unsaturated polyesters used herein can be prepared by the methods described in U.S. Pat. No's. 4,189,548, 4,167,542 and 4,148,765.

The unsaturated polyester resins suitable for use herein are well known and are described in Kirk-Othmer Encyclopedia of Chemical Technology, 3rd edition, pp. 575–594 which is incorporated herein by reference.

The unsaturated polyesteramide resins suitable for use herein are prepared by substitution of a portion of the polyol used in the unsaturated polyester resin preparation with a suitable polyamide or mixture of polyamines.

The polyols used in either unsaturated polyesters or unsaturated polyesteramides are from the class of those having the formula:

HO—R—OH where R is a divalent orgaic radical selected from the group consisting of alkylene, ether-linked alkylene, ether-linked arylene, cycloalkylene, polycycloalkylene, bis(alkyl)cycloalkylene, bis(alkyl)polycycloalkylene, and arylene. Mixtures of two or more of such polyols can also be used.

The polyamines used to make unsaturated polyesteramides are from the class of those having the formula:

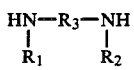

wherein $R_1$ and $R_2$ are independently selected from the group consisting of hydrogen, aliphatic, cycloaliphatic and aromatic radicals, or $R_1$ and $R_2$ taken together with the remainder of the molecule form an aliphatic ring; and $R_3$ is a divalent organic radical selected from the group consisting of alkylene, ether-linked alkylene, ether-linked arylene, alkylene amino-linked alkylene, alkylene amino-linked cycloalkylene, cycloalkylene, polycycloalkylene, arylene, alkylarylene, bis(alkyl)cycloalkylene and bis(alkyl)polycycloalkylene. Mixtures of two or more of such polyamines can also be used.

Typical diamines that are useful are ethylene diamine, propylene diamine, hexane-1,6-diamine, piperazine, 4,4'-methylenebis(cyclohexylamine), 2,2'-bis(4-aminocyclohexyl)propane, 4,4'-diaminodiphenyl ether, bis(aminomethyl)norbornane, toluene diamine, bis(aminomethyl)dicyclopentadiene and homopiperazine. Typical polyamines are aminoethylpiperazine and diethylenetriamine.

Representative of the useful diols are: ethylene glycol, propylene glycol, diethylene glycol, dipropylene glycol, dicyclopentadiene dimethanol, bis(hydroxymethyl)norbornane, methyl cyclohexanedimethanol, bis(-hydroxypropyl)bisphenol A and other hydroxyalkylated bisphenols. Typical polyols are pentaerythritol and glycerine propoxylates.

The $\alpha,\beta$-unsaturate polycarboxylic acid is preferably maleic acid, fumaric acid, the anhydride of maleic acid or mixtures of these compounds. Such acids are readily available, have good reactivity with the diol and/or the diamine, and result in products of good properties. Other less preferred unsaturated polycarboxylic acids include itaconic acid, citraconic acid, aconitic acid, teraconic acid, mesaconic acid, glutaconic acid and the like.

Part of the $\alpha,\beta$-unsaturated polycarboxylic acid may be replaced with a saturated or aromatic polycarboxylic acid to vary the crosslinking potential and physical properties of the unsaturated polyester or polyesteramide. Such acids include the aliphatic acids such as adipic acid and the aromatic acids such as isophthalic acid. Replacement of part of the $\alpha,\beta$-unsaturated acid with such acids is commonplace in the polyester art. Suitable selection of the acid and the amount necessary to achieve a desired purpose will be known to the skilled worker and can be optimized with simple preliminary experiments.

The total amount of acid varies as a function of the total polyol or mixture of polyol and polyamine and, optionally, norbornyl ingredients used.

The terminal group used to modify the unsaturated polyester or polyesteramide is a norbornyl radical. Dicyclopentadiene (DCPD) or dicyclopentadiene concentrates are most preferred norbornyl functional materials to be employed in terminating one or both ends of the chain. Polycyclopentadiene (i.e., DCPD oligomers) or dicyclopentadiene monoalcohol are also preferred species.

DCPD is sold commercially as a product of about 97 or greater percent purity. It is also sold as a $C_{10}$ hydrocarbon concentrate prepared by dimerizing a crude $C_5$ stream from the cracking of hydrocarbons as taught in U.S. Pat. No. 3,557,239.

Examples of some of the dimers which have been identified in these concentrates are the Diels-Alder adducts of two moles of isoprene (isoprene dimers), the adduct of cyclopentadiene and isoprene, the adduct of cyclopentadiene and piperylene and the like.

Either the dicyclopentadiene concentrate or the relatively pure DCPD may be employed in preparing the modified polyesters or polyesteramides.

The modified unsaturated polyesters or polyesteramides can be prepared by a variety of techniques. In a preferred method, molten $\alpha,\beta$-unsaturated carboxylic anhydride is partially hydrolyzed with less than the stoichiometric equivalent of water and reacted with the norbornyl derivative to form esters of that derivative and containing unesterified acid and anhydride. This reaction may conveniently be performed in stages whereby a reactant is added stepwise to control reaction exotherms. The product mixture is then reacted with the polyol and polyamine or the polyol alone to result in the desired modified unsaturated polyester or polyesteramide.

In a typical procedure, molten maleic anhydride and a fraction of the stoichiometric equivalent of water are maintained at an elevated temperature of from about 60° to 130° C. The initial fractional equivalent of dicyclopentadiene (DCPD) is then added and allowed to react. A second fractional equivalent of water and of DCPD is added and allowed to react. Additional fractional equivalents of DCPD are added and each allowed to react before addition of the next increment until the desired amount of DCPD has been added. The number of fractional equivalents can be increased and the size of each fractional equivalent correspondingly decreased to any desired number of fractional equivalents, including continuous addition. The relative size of the fractional equivalents can vary.

The amount of maleic (or other) anhydride employed in this first esterification step may be equal to the equivalent of DCPD in which event the product is essentially all ester. Alternatively, the amount of anhydride may be the equivalent needed to make the ester plus that excess that is to be used in the subsequent esterification or esteramidation step.

To the mixture of esterified DCPD and acid and/or anhydride is added the polyol and polyamine or the polyol alone. After addition of the polyol and polyamine or the polyol alone is complete, the reaction can be driven to maximum yield by maintaining or increasing the temperature until the desired acid number has been reached. Typically, acid numbers of 15 to 35 are preferred, with acid numbers of 15 to 25 being most preferred; although acid numbers that are higher or lower may be tolerated, and, in some instances, may be desired.

In an equally preferred method, molten $\alpha,\beta$-unsaturated carboxylic anhydride is essentially totally hydrolyzed with a stoichiometric or greater equivalent of water and reacted with the norbornyl derivative to form esters of that derivative and containing unesterified acid. This reaction may conveniently be performed in stages whereby a reactant is added stepwise, controlling reaction exotherms. The product mixture is then reacted with the polyol and polyamine or the polyol alone to result in the desired modified unsaturated polyester or polyesteramide.

In a typical procedure, molten maleic anhydride and the stoichiometric or greater equivalent of water are maintained at an elevated temperature from about 50° to 150° C. The temperature is allowed to stabilize at about 120° to 125° C. and the initial fractional equivalent of DCPD is then added and allowed to react. A second fractional equivalent of DCPD is added and allowed to react. Additional fractional equivalents of DCPD are added and each allowed to react before addition of the next increment until the desired amount of DCPD has been added.

The amount of maleic (or other) anhydride employed in this first esterification step may be equal to the equivalent of DCPD in which event the product is essentially all ester. Alternatively, the amount of anhydride may be the equivalent needed to make the ester plus that excess that is to be used in the subsequent esterification or esteramidation step.

The polyol and polyamine or the polyol alone are added to the mixture of esterified DCPD and acid as previously described.

Many other alternate methods will be recognized by the skilled worker. For example, molten maleic anhydride may be added to a mixture of DCPD and water in a reactor. The polyol and polyamine or the polyol alone are added to the mixture of esterified DCPD and acid and/or anhydride as before. Finally, although less preferred, DCPD, maleic anhydride, water and the polyol and polyamine or polyol alone may be simultaneously reacted.

The vinyl ester resins (VER) useful herein are a well-known class of resins made from unsaturated carboxylic acids and polyepoxides. Vinyl ester resins are the reaction product of about equivalent amounts of a monounsaturated monocarboxylic acid and a polyepoxide. One class of VER is described in U.S. Pat. No. 3,367,992 where dicarboxylic acid half esters of hydroxyalkyl acrylates or methacrylates are reacted with polyepoxide resins. Bowen in U.S. Pat. No's. 3,066,122 and 3,179,623 describes the preparation of VER from monocarboxylic acids such as acrylic and methacrylic acid. Bowen also describes alternate methods of preparation wherein a glycidyl methacrylate or acrylate is reacted with the sodium salt of a dihydric phenol such as bisphenol A. VER based on epoxy novolac resins are described in U.S. Pat. No. 3,301,743 to Fekete, et al. Fekete et.al. in U.S. Pat. No. 3,256,226 describe VER where the molecular weight of the polyepoxide is increased by reacting a dicarboxylic acid with the polyepoxide resin as well as acrylic acid, etc. other difunctional compounds containing a group which is reactive with an epoxide group, such as an amine, mercaptan, and the like, may be utilized in place of the dicarboxylic acid. All of the above-described resins, which contain the characteristic linkage

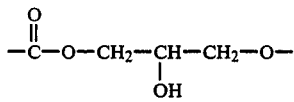

and terminal polymerizable vinylidene groups are classified as VER and are incorporated by reference.

Briefly, any of the known polyepoxides may be employed in the preparation of the vinyl ester resins. Useful polyepoxides are glycidyl polyethers of both polyhydric alcohols and polyhydric phenols, such as the diglycidyl ether of bisphenol A, epoxy novolacs, epoxidized fatty acids or drying oil acids, epoxidized diolefins, epoxidized di-unsaturated esters as well as epoxidized unsaturated polyester, so long as they contain more than one oxirane group per molecule. The polyepoxides may be monomeric or polymeric.

Preferred polyepoxides are glycidyl polyethers of polyhydric alcohols or phenols having weights per epoxide group of about 150 to 2000. The polyepoxides may be nuclearly substituted with halogen, preferably bromine. These polyepoxides are usually made by reacting at least two moles of an epiphalohydrin or glycerol dihalohydrin with one mole of the polyhydric alcohol of polyhydric phenol with a sufficient amount of a caustic alkali to combine with the halogen of the halohydrin. The products are characterized by the presence of more than one epoxide group per molecule, i.e., a 1,2-epoxy equivalency greater than one.

Vinyl ester resins are commercially available from the Dow Chemical Company under the trademark DERAKANE.

Any polymerizable ethyleneically unsaturated monomer can be used herein. Such monomers include both monovinyl and polyvinyl monomers. Typical monomers include the alkenyl aromatic monomers such as styrene, α-methylstyrene, chlorostyrene, divinylbenzene, vinyltoluene, t-butylstyrene, and the like; and alkyl and hydroxyalkyl esters of acrylic and methacrylic acid such as the methyl, ethyl, propyl, butyl, cyclohexyl, and hydroxyethyl esters. In addition to the above, other monomers that are especially useful for ultraviolet light curable systems such as 2-acetoxyalkyl acrylates, pentaerythritol di-, tri-, or tetraacrylate may be used.

Examples of polyimido-esters prepared according to this invention are the N-2-hydroxyethyl-bicyclo[2.2.1]hept-5-ene-2,3-dicarboximide, bis or tris esters of maleic, fumaric, itaconic, mesaconic, citraconic, glutaconic, tetraconic and aconitic acids. Further examples of these imido esters are the N-hydroxymethylbicyclo[2.2.1]hept-5-ene-2,3-dicarboximide, bis or tris esters of maleic, fumaric, itaconic, mesaconic, citraconic, glutaconic, teraconic and aconitic acids.

N-2-hydroxyethyl-bicyclo[2.2.1]hept-5-ene-2,3-dicarboximide, is known and can be prepared by the methods set forth in U.S. Pat. No. 2,462,835. N-hydroxymethylbicyclo[2.2.1]hept-5-ene-2,3-dicarboximide, is known and can be prepared by the methods set forth by Furdik and Sutoris in Chem. Zvesti Vol. 17(1), 31–40 (1963) and Vol. 15 (11–12), 807–814 (1961). Esterification of the unsaturated bis or tris carboxylic acid with N-2-hydroxyethyl-bicyclo[2.2.1]hept-5-ene-2,3-dicarboximide or N-hydroxymethyl-bicyclo[2.2.1]hept-5-ene-2,3-dicarboximide provides the polyimido-ester composition of this invention wherein in Formula A, m has a value of 0 and n is 2 or 1 , respectively.

Polyimido-esters wherein in Formula A, m has a value of 1 to about 10, are prepared by esterification of the bis or tris carboxylic acid with a hydroxyalkyl functional polycyclopentadienyldicarboximide derivative. As a specific example, maleic anhydride and 3 to 10 moles of cyclopentadiene are reacted by Diel-Alder addition to provide a polycyclopentadienyl carboxylic acid anhydride. Reaction of stoichiometric polycyclopentadienyl carboxylic acid anhydride with stoichiometric monoethanolamine provides the desired N-2-hydroxyethyl polycyclopentadienyl dicarboximide precursor to the polyimido-ester product.

Polyimido-ester compositions containing the structure by Formula B are prepared using the aforementioned methods. As a specific example, stoichiometric tetrahydrophthalic anhydride and stoichiometric monoethanolamine are reacted to provide the N-1-hydroxyethyl tetrahydrophthalyl functional dicarboximide precursor which is then used to esterify the unsaturated bis or tris carboxylic acid and thus provide the polyimido-ester product.

Other related compounds are prepared by using alkanolamines suc as isopropanolamine, hexanolamine, butanolamine, etc. in place of the above ethanolamine.

The resin composition, ethylenically unsaturated monomer, and imido bis or tris ester of an unsaturated di or tri carboxylic acid may be added in any order. Thus, the ethylenically unsaturated monomer or mixture of monomers may be mixed with the resin composition and then added to the imido bis or tris ester. Alternatively, the resin composition and imido bis or tris ester could be mixed first and the monomer added to the resulting mixture. Finally, the resin composition may be added to a mixture of the monomer and imido bis or tris ester.

The final blend is a crosslinkable unsaturated polyester, unsaturated polyesteramide, dicyclopentadiene modified unsaturated polyester, dicyclopentadiene modified unsaturated polyesteramide, vinyl ester resin or mixture thereof; ethylenicaly unsaturated monomer; and imido bis or tris ester of an unsaturated di or tri carboxylic acid which is useful to make laminate, castings, or coatings.

The laminates of this invention are made by mixing, into the crosslinkable composition, free radical forming curing agents in known amounts and adding this mixture to a suitable fibrous reinforcement such as asbestos fibers, carbon fibers, fibrous glass, or inorganic fibers.

Suitable curing agents which can be employed to cure the compositions of the present invention include, for example, free radical forming catalysts. Examples of these catalysts are benzoyl peroxide, tertiary butyl hydroperoxide, methylethyl ketone peroxide, and the like. It is frequently of value to add accelerators such as cobalt naphthenate, dimethylaniline, and the like.

The resin is rolled, sprayed, or impregnated into the fibrous reinforcement such as fibrous glass and cured in a manner well known in the art. When fibrous glass is used, it can be in any form such as chopped strands, filaments, glass ribbons, glass yarns, or reinforcing mats. The resin may be compounded with solvents, pigments, or other resinous products and cured to form useful coatings in a manner well known in the art.

The following examples are illustrative of the invention but are not to be construed as to limiting the scope thereof in any manner. EXAMPLE 1

Preparation of
N-2-hydroxyethyl-bicyclo[2.2.1]hept-5-ene-2,3-dicarboximide, bis ester of fumaric acid Monoethanolamine (1.00 moles, 61.08 grams) was added to a stirred reactor maintained under a nitrogen atmosphere and heated to 90° C. Endomethylenetetrahydrophthalic anhydride [cis-5-norbornane-endo-2,3-dicarboxylic acid anhydride] (1.00 moles, 164.15 grams) was added over a twenty-minute period, then the stirred solution was heated to 110° C. with nitrogen sparging (0.5 liter per minute) and the steam condenser was started. After a total of 17.5 milliliters of water layer was collected in the Dean Stark trap, the acid number was 2.3. At this time, fumaric acid (0.50 mole, 58.04 grams) and tin oxide (SnO) catalyst (0.15 weight percent, 0.37 grams) were added and the temperature controller was set at 205° C. After 4.0 hours at the 205° C. reaction temperature, the temperature controller was set at 225° C. and this temperature was maintained until an additional 15.0 milliliters of water was collected in the Dean Stark trap. The reactor was cooled to 160° C. and 100 ppm of hydroquinone was added. N-2-hydroxyethyl bicyclo[2.2.1]-hept-5-ene-2,3-dicarboximide bis ester of fumaric acid was recovered as a light amber-colored solid in 99% yield.

EXAMPLE 2

Preparation of N-2-hydrocyethyl bicyclo(2.2.1)hept-5-ene-2,3-dicarboximide bis ester of fumaric acid using in situ generated cyclopentadiene Dicyclopentadiene (1.04 moles 137.2 grams) was added to a reactor and heated to 75° C. with stirring. Powdered maleic anhydride (2.0 moles 197.2 grams) was added to the reactor then the temperature controller was set at 165° C. After eleven hours of reaction at 165° C., gas chromatographic analysis demonstrated the presence of only 2.6 percent by weight unreacted maleic anhydride and 2.0 percent by weight unreacted dicyclopentadiene. At this time, the reactor was cooled to 150° C., then monoethanolamine (2.0 moles 122.2 grams) was added dropwise inducing a maximum exotherm of 165° C. After 3.5 hours of reaction at 165° C., an acid number of 4.5 was obtained. At this time, the reactor was cooled to 95° C. then maleic anhydride (1.0 mole 98.6 grams), water (2.00 moles 36.0 grams), stannous oxide [esterification catalyst] (0.1 percent by weight 0.568 gram) and potassium thiocyanate [isomerization catalyst] (1.0 percent by weight 5.68 grams) were added. The reaction was continued for 2 hours at 95° C. then the temperature controller was set at 182° C. Once the 182° C. reaction temperature was achieved, water was continuously removed from the reactor through a steam condensor—Dean Stark trap—cold water condenser assembly. Once an acid number of 15 was achieved, the reactor was cooled to 160° C. and 100 ppm of hydroquinone was added. N-2-hydroxyethyl bicyclo(2.2.1)hept-5-ene-2,3-dicarboximide bis ester of fumaric acid (492.8 grams) was recovered as an amber-colored solid.

EXAMPLE 3

About 1 equivalent of methacrylic acid is reacted with 0.75 equivalent of an epoxy novolac having an epoxide equivalent weight (EEW) of 175–182 and 0.25 equivalent of a glycidyl polyether of bisphenol A having an EEW of 186–192. The above reactants are heated to 115° C. with catalyst and hydroquinone present until the carboxylic acid content reaches about 1 percent. The reactants are cooled and then styrene (containing 50 ppm of t-butyl catechol) is added. The final vinyl ester resin diluted with styrene has a pH of 7.7 and contains approximately:

| Contents | % |
| --- | --- |
| styrene | 36 |
| methacrylic acid | 20.6 |
| epoxy novolac (EEW = 175-182) | 32.1 |
| diglycidyl ether of bisphenol A (EEW = 186-192) | 11.3 |
| | 100.0 |

A portion of the styrenated vinyl ester resin (300.0 grams) and a portion of the N-2-hydroyethylbicyclo[2.2.1]hept-5-ene-2,3-dicarboximide, bis ester of fumaric acid (33.35 grams) from Example 1 were formulated to provide a 10.0% solution of the amido ester. This solution was used to prepare a laminate in accordance with th following standard hand lay-up procedure:

A sheet of 0.005 inch Mylar film was attached to a smooth flat surface with masking tape. An area of sufficient size was covered with a thin coating of the laminating resin and a surfce of C-veil from Owens Corning Fiberglass Corporation was laid down and smoothed out. Additional resin was applied and the first layer of 1.5 ounce chopped fiberglass mat having a surface coupling agent was applied. This was carefully rolled down with a serrated aluminum roller to exclude all trapped air. Resin was added, followed by a second layer of 1.5 ounce chopped fiberglass mat. Rolling again removed any entrapped air. After adding additional resin, the final surface C-veil was applied and smoothed out. Straight steel rails of ⅛ inch square in cross-section were placed along all four sides of the laminate. A cover sheet of Mylar was rolled onto a 2-inch dimaeter tube long enough to bridge the rails. Additional resin was added to the laminate and the Mylar was rolled out over it. The Mylar was then stretched tightly and taped down. Any entrapped air or excess resin was squeezed out of the laminate using a wooden tongue depressor. The laminate was left until the polymerization exotherm had subsided and cooling to ambient temperature had occurred. The laminate was removed and post-cured at 100° C. for 2.0 hours.

A cure system of 1.0 percent methylethylketone peroxide and 0.3 percent cobalt naphthenate (6.0%) was used for the laminate. A series of 15 standard flexural test pieces were cut from the laminate and sorted to provide 5 serialized groups of three pieces each. Four groups of test pieces were weighed and then placed on a flat aluminum tray. The tray was suspended in a vented forced-air convection-type oven maintained at 100° C. After 2.0 hours at the 100° C. temperature, the temperature was increased to 150° C. for 1 hour then 200° C. for 2 hours and finally 240° C. for the duration of the 720 hour heat exposure test. The test pieces were removed and weighed after the hours of exposure indicated in Table 1. The remaining test pieces were used as standards (no exposure to the 240° C. test temperature). All test pieces were visually inspected during and after removal from the test. Flexural strength and flexural modulus were determined at the zero, 72, 168, 336, and 720 hour exposure intervals using the Instron machine with standard methods (ASTM D-790). All Barcol hardness values are on the 934-1 scale. Weight loss (percent) was determined by weighing of the test pieces both before and after the indicated thermal exposure. The results are reported in Table I.

Control 1—A portion of the styrenated vinyl ester resin of Example 3 was used to prepare a laminate using the method of Example 3 but without the imido-ester. Heat exposure of test pieces prepared from the laminate was simultaneous with that of Example 3. The results using no imido-ester are reporated in Table 1 as the number or evaluation in parenthesis.

Table I illustrates that the use of the bis imido ester of fumaric acid in Example 3 has significantly decreased the percent weight loss, decreased the time to and extent of delamination, and increased both the initial flexural strength and modulus values as well as their retention as a function of thermal exposure time, when compared to Control 1.

TABLE 1

| | Hours of Exposure to 240° C.* | | | | | |
| --- | --- | --- | --- | --- | --- | --- |
| | None | 24 | 72 | 168 | 336 | 720 |
| Barcol Hardness | 50 | NA | 52 | 58 | 60 | 61 |
| | (49) | (NA) | (50) | (52) | (54) | (53) |
| Weight Loss (%) | 0 | −1.29 | −2.04 | −2.96 | −3.86 | −5.24 |
| | (0) | (−1.68) | (−2.58) | (−3.76) | (−5.14) | (−8.06) |
| Flexural Strength ×10³ (psi) | 15.3 | NA | 14.7 | 15.3 | 14.5 | 16.2 |
| | (12.3) | (NA) | (10.4) | (12.7) | (12.1) | (12.2) |
| Flexural Modulus ×10⁵ (psi) | 10.4 | NA | 9.4 | 9.0 | 8.9 | 8.6 |
| | (9.3) | (NA) | (8.2) | (7.8) | (7.9) | (6.9) |
| Delamination | 0 | None | None | Very slight | Very slight | Very slight (Severe delamination and surface pitting) |
| | (0) | (Very slight) | (Moderate) | (Moderate) | (Moderate to severe) | |

Notes:
*All samples darken after 4 hours of exposure, otherwise no other visually observable changes occurred at that time.
Values in parenthesis are for Control 1.

EXAMPLE 4

Maleic anhydride (7.0 moles, 686.42 grams) was added to a reactor and heated to 100° C. under a nitrogen atmosphere. Water (7.1 moles, 127.94 grams) was added to the reactor. A maximum exotherm of 131° C. resulted two minutes later, followed by a decrease in the reaction temperature to 121° C. fifteen minutes after the initial water addition. At this time, dicylopentadiene (2.10 moles, 277.64 grams) of 97 percent purity was added. A maximum exotherm of 125° C. resulted two minutes later with a 120° C. temperature being established two minutes after the initial dicyclopentadiene addition. Fifteen minutes after the initial addition of dicyclopentadiene, a second portion of dicyclopentadiene (2.10 moles, 277.64 grams) was added. Fifteen minutes later, a final aliquot of dicyclopentadiene (2.10 moles, 277.64 grams) was added and the temperature controller was maintained at 120° C. This temperature was re-established three minutes later. After 30 minutes, propylene glycol (3.78 moles, 287.66 grams) and piperazine (0.420 mole, 36.18 grams) were added to the reactor and the steam condenser was started, nitrogen sparging was increased to 0.75 liter per minute, and the temperature controller was set at 160° C. The 160° C. temperature was reached twenty-five minutes later. After two hours at 160° C., the temperature controller was set at 205° C., and this temperature was achieved twenty-eight minutes later. After 14.0 hours, a total of 151 milliliters of water layer and 28 milliliters of organic material were collected in the Dean Stark trap. The reactor was cooled to 165° C. and 100 ppm of hydroquinone was added. The dicyclopentadiene modified unsaturated polyesteramide alkyd was recovered as a clear, light yellow-colored solid with a final acid number of 18.9.

A portion of the modified unsaturated polyesteramide alkyd (182.0 grams), styrene (133.0 grams), and a portion of the N-2-hydroxyethyl bicyclo[2.2.1]hept-5-ene-2,3-dicarboximide, bis ester of fumaric acid (35.0 grams) from Example 1 were formulated to provide a 52.0, 38.0, 10.0 percent solution, respectively. This solution was used to determine Brookfield viscosity (25° C.), SPI gel characteristics (84° C.), average Barcol hardness (934-1 scale), and a clear, unfilled ⅛ inch casting was made for heat distortion temperature (264 psi), tensile and flexural strength, flexural modulus, and percent elongation determinations. The clear casting was prepared using a cure system of 1.0 percent benzoyl peroxide and 0.05 percent N,N-dimethylaniline at room temperature (25° C.), followed by postcuring for 2.0 hours at 100° C. Mechanical properties of tensile (6) and flexural (6) test pieces were determined using an Instron machine with standard test methods (ASTM D-638 and D-790). Heat distortion temperature of clear casting test pieces (2) was determined using an Aminco Plastic Deflection Tester (American Instrument Co.) with standard test methods (ASTM D-648 modified). The results are reported in Table 2.

Control 2—A portion of the modified unsaturated polyesteramide alkyd (199.5 grams) of Example 4 and styrene (150.5 grams) were formulated to provide a 57.0, 43.0 percent solution, respectively. The physical and mechanical properties of the resin formulation were determined using the method of Example 4. The results are reported in Table 2.

TABLE 2

|  | Example 4 | Control 2 |
|---|---|---|
| Brookfield Viscosity (cp) | 429 | 184 |
| SPI Gel Test |  |  |
| Gel time (min) | 2.6 | 2.7 |
| Cure time (min) | 4.6 | 4.9 |
| Maximum Exotherm (°C.) | 215 | 221 |
| Average Barcol Hardness | 46 | 46 |
| Heat Distortion Temperature (°F.) | 235 | 239 |
| Tensile Strength $\times 10^3$ (psi) | 4.2 | 5.1 |

TABLE 2-continued

|  | Example 4 | Control 2 |
|---|---|---|
| Elongation (%) | 0.8 | 1.1 |
| Flexural Strength $\times 10^3$ (psi) | 10.1 | 14.5 |
| Flexural Modulus $\times 10^5$ (psi) | 6.1 | 5.9 |

EXAMPLE 5

A pair of heat distortion temperature test pieces were prepared from the clear unfilled casting of Example 4. The test pieces were weighed and then placed on a flat aluminum tray and suspended in a vented, forced-air, convection-type oven. Additional post curing was completed at 150° C. for 1.0 hour then 175° C. for 1.0 hour followed by heat aging at 240° C. for the hours of exposure indicated in Table 3. Both test pieces were weighed and visually inspected at the specified exposure interval. Heat distortion temperature and Barcol hardness were determined using the method of Example 4. The results are reported in Table 3.

Control 3—A pair of heat distortion temperature test pieces were prepared from the clear unfilled casting of Control 2. Testing was performed using the method of Example 5. Exposure to the 240° C. test temperature was simultaneous with that of Example 5. The results are reported in Table 3 as the information in parenthesis.

Table 3 illustrates that the use of the bis imido ester of fumaric acid in Example 5 has substantially increased heat distortion temperature and decreased the time to and extent of surface crazing as a function of thermal exposure time, when compared to Control 3.

TABLE 3

|  | Hours of Exposure to 240° C.* | | | | | |
|---|---|---|---|---|---|---|
|  | None | 24 | 48 | 168 | 336 | 672 |
| Barcol Hardness | 46 | NA | NA | NA | NA | 47 |
|  | (46) | (NA) | (NA) | (NA) | (NA) | (49) |
| Weight Loss (%) | 0 | −1.47 | −1.95 | −3.74 | −5.21 | −7.24 |
|  | (0) | (−1.59) | (−2.16) | (−4.20) | (−5.86) | (−7.96) |
| Heat Distortion | 235 | NA | NA | NA | NA | 370 |
| Temperature (°F.) | (239) | (NA) | (NA) | (NA) | (NA) | (321) |
| Visual Observation | 0 | none | none | none | none (slight | |
|  | (0) | (none) | (none) | (none) | surface crazing) | |

Note:
*All samples darking after 24 hours of exposure.
1 very slight surface crazing
(1) moderate surface crazing.

EXAMPLE 6

A portion of the vinyl ester resin (300.0 grams) of Example 3 and N-2-hydroxyethyl-bicyclo[2.2.1-]-hept-5-ene-2,3-dicarboximide, bis ester of fumaric acid (33.35 grams) of Example 2 were formulated to provide a 10.0 percent solution of the fumarate in the vinyl ester resin. This solution was used to prepare a laminate using the method of Example 3.

A series of 16 standard flexural test pieces were cut from the laminate and sorted to provide 4 serialized groups of four pieces each. Three groups of test pieces were weighed and then placed on a flat aluminum tray. The tray was suspended in a vented forced-air convection-type oven maintained at 245° C. The test pieces were removed and weighed after the hours of exposure indicated in Table 4. The remaining test pieces were used as standards (no exposure to the 245° C. test temperature). All test pieces were visually inspected during and after removal from this test. Flexural strength and flexural modulus were determined at the zero, 168, 326 and 720 hour exposure intervals using an Instron machine with standard methods (ASTM D-790). All Barcol hardness values are on the 934-1 scale. Weight loss (percent) was determined by weighing of the test pieces both before and after the indicated thermal exposure. The results are reported in Table 4.

Control 4—A portion of the styrenated vinyl ester resin of Example 3 was used to prepare a laminate using the method of Example 3. Exposure of the test pieces prepared from the laminate was simultaneous with that of Example 6. The results are reported in Table 4 as the information in parenthesis.

The use of the bis imido ester of fumaric acid in Example 6 has significantly decreased the percent of weight loss, decreased the time to and extent of delamination, and increased both the initial flexural strength and modulus values as well as their retention as a function of thermal exposure time, when compared to Control 4.

TABLE 4

| | Hours of Exposure to 245° C.* | | | |
|---|---|---|---|---|
| | None | 168 | 326 | 720 |
| Barcol Hardness | 51 | 59 | 58 | 56 |
| | (49) | (56) | (59) | (56) |
| Weight Loss (%) | 0 | −3.75 | −4.96 | −7.23 |
| | (0) | (−4.74) | (−7.92) | (−14.73) |
| Flexural Strength | 14.4 | 15.7 | 13.5 | 13.6 |
| ×10³ (psi) | (13.0) | (12.3) | (12.5) | (11.7) |
| Flexural Modulus | 9.4 | 8.1 | 8.2 | 6.9 |
| ×10⁵ (psi) | (9.0) | (7.8) | (7.7) | (5.5) |
| Delamination | 0 | slight (moderate) | slight (severe with pitting) | moderate (severe with pitting) |

Notes:
*All samples darken after 4 hours of exposure, otherwise no other visually observable changes occurred at that time.
Control 4 values are in parenthesis.

I claim:

1. A thermosettable resin composition which comprises (A) about 5 to about 95 percent by weight based on the total composition weight of at least one resin selected from the group consisting of (a) unsaturated polyester resins, (b) unsaturated polyesteramide resins, (c) dicyclopentadiene modified unsaturated polyester resins, (d) dicyclopentadiene modified unsaturated polyesteramide resins, and (e) vinyl ester resins, (B) about 5 to about 95 percent by weight of at least one polymerizable ethylenically unsaturated monomer; and (C) about 1 to about 70 percent by weight of an imido-ester compound having the formula

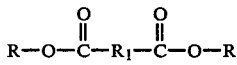

wherein R is selected fom one of the following groups

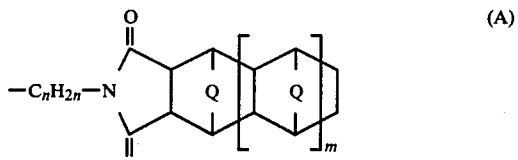

(A)

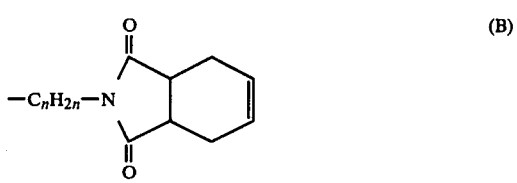

(B)

and $R_1$ is a divalent radical selected from one of the following groups

I. $-C(X)=CH-$
II. $-CH_2-C(=Y)-$
III. $-CH=C(Z)-CH_2-$ wherein
$n = 1-6$
$m = 0-10$
X = hydrogen or methyl
Y = methylene or isopropylidene
Z = hydrogen or $-COOR$
Q = methylene.

2. A thermosettable resin composition which comprises (A) about 5 to about 95 percent by weight based on the total composition weight of at least one resin selected from the group consisting of (a) unsaturated polyester resins, (b) unsaturated polyesteramide resins, (c) dicyclopentadiene modified unsaturated polyester resins, (d) dicyclopentadiene modified unsaturated polyesteramide resins, and (e) vinyl ester resins, (B) about 5 to about 95 percent by weight of at least one polymerizable ethylenically unsaturated monomer; and (C) about 1 to about 70 percent by weight of an imido-ester compound having the formula

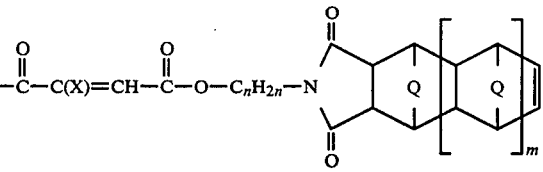

where,
$n = 1-6$
$m = 0-10$
X = hydrogen or methyl
Q = methylene.

3. A themosettable resin composition which comprises (A) about 5 to about 95 percent by weight based on the total composition weight of at least one resin selected from the group consisting of (a) unsaturated polyester resins, (b) unsaturated polyesteramide resins, (c) dicyclopentadiene modified unsaturated polyester resins, (d) dicyclopentadiene modified unsaturated polyesteramide resins, and (e) vinyl ester resins, (B) about 5 to about 95 percent by weight of at least one polymerizable ethylenically unsaturated monomer; and (C) about 1 to about 70 percent by weight of an imido-ester compound having the formula

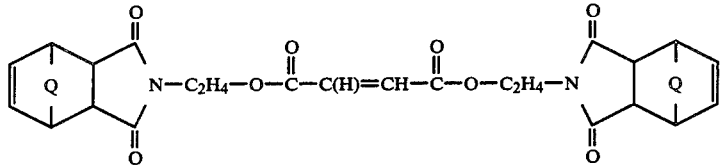

where

Q=methylene.

4. A cured fibrous laminate made with the composition of claim 1.

5. A cured fibrous laminate made with the composition of claim 2.

6. A cured fibrous laminate made with the composition of claim 3.

* * * * *

UNITED STATES PATENT AND TRADEMARK OFFICE
CERTIFICATE OF CORRECTION

PATENT NO. : 4,640,957

DATED : February 3, 1987

INVENTOR(S) : Robert E. Hefner, Jr. and Douglas L. Hunter

It is certified that error appears in the above-identified patent and that said Letters Patent is hereby corrected as shown below:

Col. 1, lines 48-54; insert a double bond into the formula so that the formula is the same as the formula (RH end) in Claim 2(c).

COl. 2, line 62; change "polyamide" to --polyamine--.

Col. 3, line 1; change "orgaic" to --organic--.

Col. 3, line 39; change "α,β-unsaturate" to --α,β-unsaturated--.

Col. 6, line 45; change "tetraconic" to --teraconic--.

Col. 6, line 66; change "polycyclopentadienyldicarboximide" to --polycyclopentadienyl dicarboximide--.

Col. 7, line 11; change "N-1-hydrox-" to --N-2-hydrox- --.

Col. 7, line 34; change "ethylenicaly" to --ethylenically--.

Col. 7, line 36; change "laminate," to --laminates,--.

Col. 8, line 22; change "N-2-hydrocyethyl" to --N-2-hydroxyethyl--.

UNITED STATES PATENT AND TRADEMARK OFFICE
CERTIFICATE OF CORRECTION

PATENT NO. : 4,640,957

DATED : February 3, 1987

INVENTOR(S) : Robert E. Hefner, Jr. and Douglas L. Hunter

It is certified that error appears in the above-identified patent and that said Letters Patent is hereby corrected as shown below:

Col. 9, line 15; change "th" to --the--.

Col. 9, line 20; insert --the-- between "from" and "Owens".

Col. 10, line 19; change "reporated" to --reported--.

Col. 14, lines 2-8; insert a double bond into the formula so that the formula is the same as the formula (RH end) in Claim 2(c).

Signed and Sealed this

Eighth Day of September, 1987

Attest:

DONALD J. QUIGG

*Attesting Officer*  *Commissioner of Patents and Trademarks*

UNITED STATES PATENT AND TRADEMARK OFFICE
CERTIFICATE OF CORRECTION

PATENT NO. : 4,640,957
DATED : February 3, 1987
INVENTOR(S) : Robert E. Hefner, Jr. and Douglas L. Hunter It is certified that error appears in the above-identified patent and that said Letters Patent is hereby corrected as shown below:

Col. 1, lines 26; change "4,450,634" to -- 4,480,077--

Signed and Sealed this

Twenty-first Day of June, 1988

Attest:

DONALD J. QUIGG

Attesting Officer

Commissioner of Patents and Trademarks